United States Patent
Jackson et al.

(10) Patent No.: US 9,648,876 B2
(45) Date of Patent: May 16, 2017

(54) METHOD OF INHIBITING BIOFILM FORMATION

(71) Applicant: Research Foundation of the City University of New York, New York, NY (US)

(72) Inventors: Desmond N. Jackson, New York, NY (US); Edward N. Kennelly, Bronx, NY (US); Peter Lipke, Brooklyn, NY (US)

(73) Assignee: Research Foundation of City University of New York, New York, NY (US)

( * ) Notice: Subject to any disclaimer, the term of this patent is extended or adjusted under 35 U.S.C. 154(b) by 0 days.

(21) Appl. No.: 15/137,692

(22) Filed: Apr. 25, 2016

(65) Prior Publication Data

US 2016/0309711 A1  Oct. 27, 2016

Related U.S. Application Data

(60) Provisional application No. 62/152,409, filed on Apr. 24, 2015.

(51) Int. Cl.
*A61K 31/12* (2006.01)
*A01N 35/06* (2006.01)
*A01N 49/00* (2006.01)
*A01N 65/36* (2009.01)
*A01N 43/653* (2006.01)

(52) U.S. Cl.
CPC ............ *A01N 35/06* (2013.01); *A01N 49/00* (2013.01); *A01N 65/36* (2013.01); *A01N 43/653* (2013.01)

(58) Field of Classification Search
CPC ....... A61K 31/12; A01N 35/06; A01N 43/653
See application file for complete search history.

(56) References Cited

PUBLICATIONS da Rosa et al (PNAS, Jan. 26, 2010, vol. 107, No. 4, pp. 1594-1599).*
Hemshekhar et al (Phytochem Rev, 2011, 10:325-351).*
Klepser et al (Antimicrobial Agents and Chemotherapy, Jun. 1997, vol. 41, No. 6, pp. 1392-1395).*
Roux, D. et al.; Structure-Activity Relationship of Polyisoprenyl Benzophenones from Garcinia pyrifera on the Tubulin/Microtubule System; Journal of Natural Products; Jun. 30, 2000; pp. 1070-1076; vol. 63, No. 8; American Chemical Society and American Society of Pharmacognosy.
Jackson, D. et al.; Garcinia xanthochymus Benzophenones Promote Hyphal Apoptosis and Potentiate Activity of Fluconazole against Candida albicans Biofilms; Antimicrobial Agents and Chemotherapy; Oct. 2015; pp. 6032-6038; vol. 59, No. 10.
Varalakshmi, K.N. et al.; Antimicrobial and Cytotoxic Effects of Garcinia Indica Fruit Rind Extract; American-Eurasian J. Agric. & Environ. Sci.; 2010; pp. 652-656; vol. 7, Issue 6; IDOSI Publications.
Matsumoto, K. et al.; Cytotoxic Benzophenone Derivatives from Garcinia Species Display a Strong Apoptosis-Inducing Effect against Human Leukemia Cell Lines; Biol. Pharm. Bull.; Apr. 2003; pp. 569-570; vol. 26, No. 4; Pharmaceutical Society of Japan.
Simonetti, G. et al.; Histone deacetylase inhibitorsmay reduce pathogenicity and virulence in Candida albicans; Federation of European Microbiological Societies; Jul. 12, 2007; pp. 1371-1380; vol. 7; Blackwell Publishing Ltd.
Dahlin, J. et al.; A Cell-Free Fluorometric High-Throughput Screen for Inhibitors of Rtt109-Catalyzed Histone Acetylation; PLOS One; Nov. 2013; pp. 1-15; vol. 8, Issue 11.
Balasubramanyam, K. et al; Polyisoprenylated Benzophenone, Garcinol, a Natural Histone Acetyltransferase Inhibitor, Represses Chromatin Transcription and Alters Global Gene Expression; The Journal of Biological Chemistry; May 19, 2004; pp. 33716-33726; vol. 279, Issue 32; The American Society for Biochemistry and Molecular Biology, Inc.

* cited by examiner

*Primary Examiner* — Sudhakar Katakam
(74) *Attorney, Agent, or Firm* — Peter J. Mikesell; Schmeiser, Olsen & Watts, LLP

(57) ABSTRACT

Xanthochymol and garcinol, isoprenylated benzophenones purified from *Garcinia xanthochymus* fruits, showed multiple activities against fungal biofilms. Both compounds effectively prevented emergence of fungal germ tubes and were also cytostatic, with MICs of 1 to 3 ΞM. The compounds therefore inhibited development of hyphae and subsequent biofilm maturation. Xanthochymol treatment of developing and mature biofilms induced cell death. In early biofilm development, killing had the characteristics of apoptosis. These activities resulted in failure of biofilm maturation and hyphal death in mature biofilms. In mature biofilms, xanthochymol and garcinol caused the death of biofilm hyphae, with 50% effective concentrations ($EC_{50}$s) of 30 to 50 μM. Additionally, xanthochymol-mediated killing was complementary with fluconazole against mature biofilms, reducing the fluconazole $EC_{50}$ from greater than 1,024 μg per ml to 13 μg per ml.

17 Claims, 2 Drawing Sheets

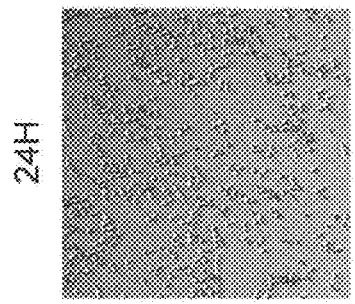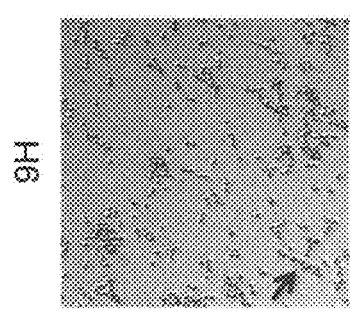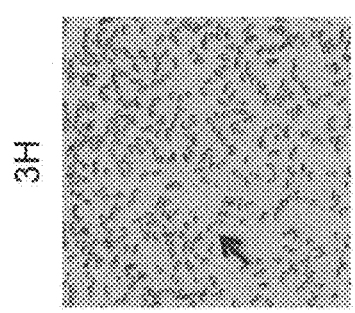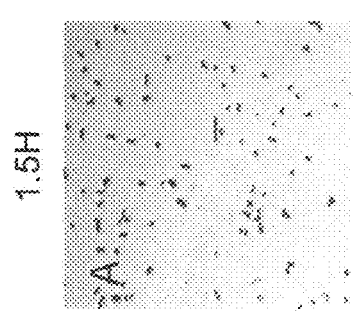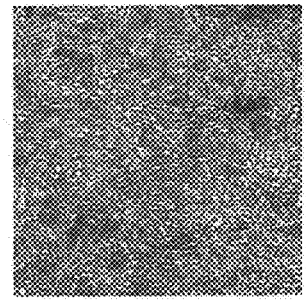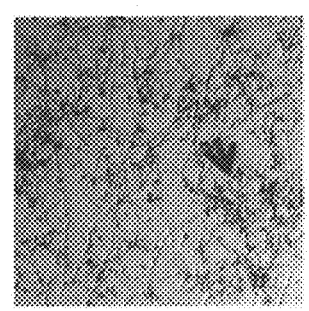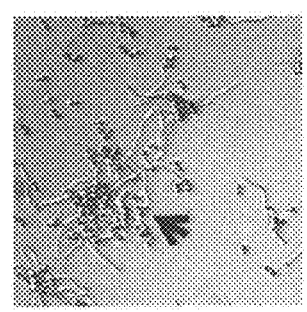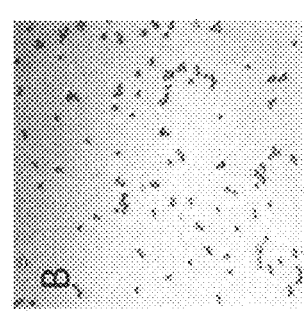

METHOD OF INHIBITING BIOFILM FORMATION

CROSS-REFERENCE TO RELATED APPLICATIONS

This application claims priority to and is a non-provisional of U.S. Patent Application Ser. No. 62/152,409, (filed Apr. 24, 2015), the entirety of which is incorporated herein by reference.

STATEMENT OF FEDERALLY SPONSORED RESEARCH OR DEVELOPMENT

This invention was made with Government support under grant number R01GM098616 awarded by the U.S. Public Health Service. The government has certain rights in the invention.

BACKGROUND OF THE INVENTION

The subject matter disclosed herein relates to method for reducing fungal infections and specifically to a method for reducing fungal infections by killing fungi at the hyphal stage.

Disseminated *Candida albicans* infections represent a growing cause of morbidity and mortality, especially among immunocompromised individuals, surgical patients, and those with implanted medical devices. *Candida albicans* is a dimorphic fungus capable of existing as a commensal species on skin and mucus membranes of humans. The fungus spends most of its life in the form of multicellular communities called biofilms, heterogeneous mixtures of yeast, hyphae, and pseudohyphal forms embedded in a complex extracellular matrix. The plasticity of *C. albicans* growth is associated with the virulence of the organism. For instance, the hyphal form of the fungus is capable of invading and disrupting epithelial and endothelial cells, resulting in disseminated disease. Progression of disease is also a function of *C. albicans* dimorphism, since hyphae enable escape from macrophages. Fungal attachment and biofilm development contaminate implanted medical devices, necessitating removal of the devices to prevent dissemination. In biofilms, the fungus is refractory to removal by drug intervention or the host immune system. Indeed, numerous studies have associated biofilm formation with increasing drug resistance. Multiple factors underlie the increased drug resistance observed in biofilms. These include upregulation of drug efflux pumps as well as biofilm architecture that results in differences in abundance of drug targets and metabolism within the biofilm community. Further complicating the picture is the secretion of the extracellular matrix, which can function to impede the penetration of drugs throughout the biofilm. Concomitant with increasing drug resistance of *C. albicans* isolates, there is a dearth of drugs and drug targets for the treatment of systemic candidiasis. All current antifungal treatments target an extremely small part of the fungal genome. It is therefore desirable to find new phytochemicals and methods that provide protection from fungal infections. The discussion above is merely provided for general background information and is not intended to be used as an aid in determining the scope of the claimed subject matter.

BRIEF DESCRIPTION OF THE INVENTION

Xanthochymol and garcinol, isoprenylated benzophenones purified from *Garcinia xanthochymus* fruits, showed multiple activities against fungal biofilms. Both compounds effectively prevented emergence of fungal germ tubes and were also cytostatic, with MICs of 1 to 3 µM. The compounds therefore inhibited development of hyphae and subsequent biofilm maturation. Xanthochymol treatment of developing and mature biofilms induced cell death. In early biofilm development, killing had the characteristics of apoptosis, including externalization of phosphatidyl serine and DNA fragmentation, as evidenced by terminal deoxynucleotidyltransferase-mediated dUTP-biotin nick end labeling (TUNEL) fluorescence. These activities resulted in failure of biofilm maturation and hyphal death in mature biofilms. In mature biofilms, xanthochymol and garcinol caused the death of biofilm hyphae, with 50% effective concentrations ($EC_{50}$s) of 30 to 50 µM. Additionally, xanthochymol-mediated killing was complementary with fluconazole against mature biofilms, reducing the fluconazole $EC_{50}$ from greater than 1,024 µg per ml to 13 µg per ml. The method may be used an anti-fungal therapeutic or as a prophylactic dosing. In one embodiment, the combination of the catechol and fluconazole reduces the $EC_{50}$ of the combination by at least 50% relative to the $EC_{50}$ of fluconazole alone (e.g. from 1,024 µg per ml to less than 512 µg per ml).

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 1A, FIG. 1B, FIG. 1C and FIG. 1D are images of fungi after exposure to xanthochymol at 1.5 hours, 3 hours, 9 hours and 24 hours, respectively;

FIG. 2A, FIG. 2B, FIG. 2C and FIG. 2D are images of fungi in the absence of xanthochymol at 1.5 hours, 3 hours, 9 hours and 24 hours, respectively.

DETAILED DESCRIPTION OF THE INVENTION

Figure 3:
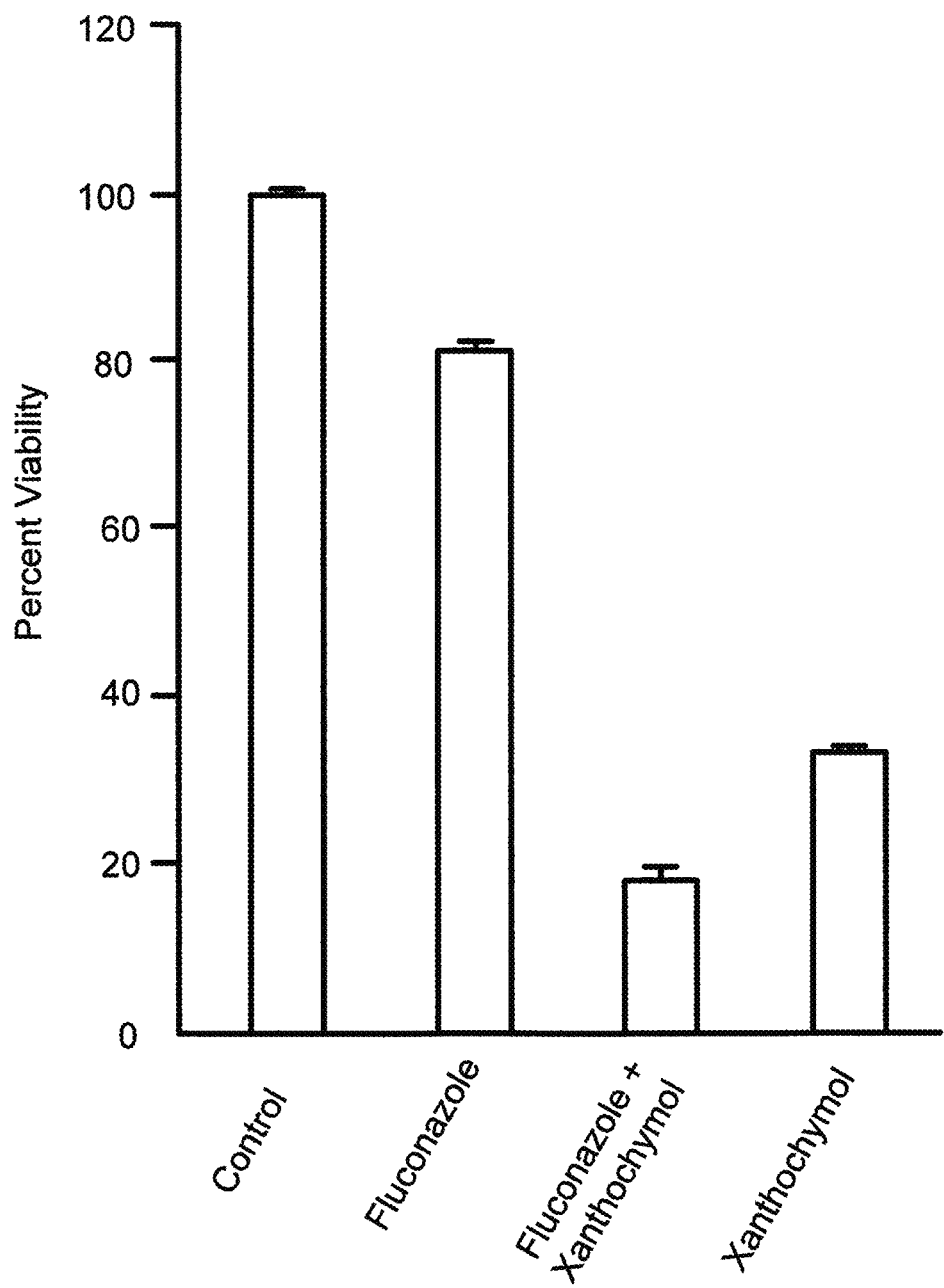
FIG. 3 is a graph showing the effects of a combination of xanthochymol and fluconazole on fungi viability.

Xanthochymol and garcinol, stereoisomeric multi-isoprenylated benzophenones from the fruit of *Garcinia xantho-*

*chymus*, have been identified as potential antibiofilm agents. Xanthochymol and garcinol are catechols, compounds containing a 1,2-benzenediol moiety. These compounds can be extracted from the fruit in high concentrations (up to 70 mg per g dry mass). Both xanthochymol and garcinol were cytotoxic to *C. albicans* biofilms and specifically targeted the hyphal form of the fungus.

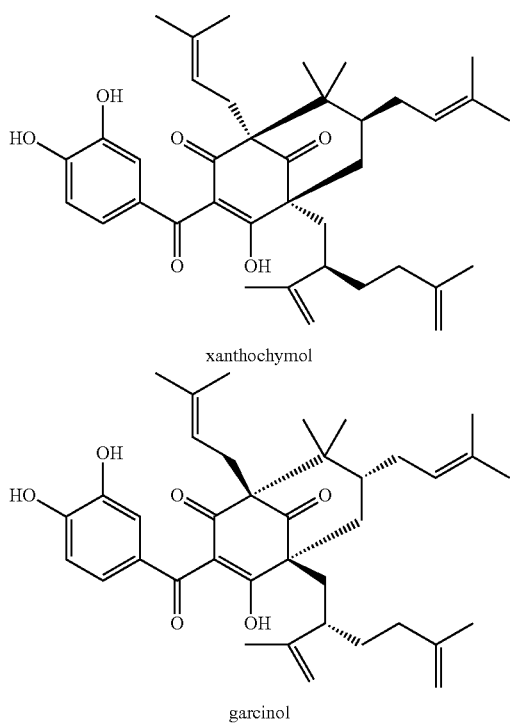

xanthochymol garcinol

Xanthochymol and garcinol showed multiple activities against *C. albicans* biofilms. In temporal order, these activities included inhibition of hyphal emergence, inhibition of microcolony formation, proapoptotic activity early in biofilm formation, hyphal cytotoxicity in mature biofilms, and complementarity to the activity of fluconazole.

In vitro growth of *C. albicans* hyphae proceeds in two phases: in the first several hours, germ tubes are produced; then they are extended to form true hyphae, which must be maintained long term. This process is under tight transcriptional regulation and is also dependent on chromatin remodeling). A transcription complex between Tup1 and Nrg1 represses the initiation of transcription of hypha-specific genes. Induction signals transmitted through the cyclic AMP-protein kinase A (PKA) pathway result in loss of Nrg1 repression, followed by exchange of chromosomal remodeling enzymes, with the histone acetylase NuA4 dissociating and the histone deacetylase complex (HDAC) component Hda1 newly binding to the promoter region. Hda1 prevents rebinding of Nrg1 to hyphal promoters, probably by chromatin remodeling. The inhibitory effects of garcinol and xanthochymol on germ tube emergence imply that the compounds interfere with this program. Xanthochymol was effective at concentrations as low as 4 to 8 μg per ml (FIG. 3).

Both garcinol and xanthochymol are known to display biological activity against methicillin-resistant *Staphylococcus aureus* (MRSA). These compounds are also known to induce apoptosis in numerous human cancer cell lines, including leukemia and breast, prostate, colon, and pancreatic cancer cell lines. Garcinol inhibits histone acetyltransferase (HAT) p300 and pCAF at micromolar concentrations. In *C. albicans*, garcinol inhibits HAT Rtt109-catalyzed histone acetylation. Inhibition of microtubule disassembly into tubulin by xanthochymol has also been reported. Extracts from *Garcinia* species have antifungal activity against planktonic *C. albicans*, but only at the relatively high concentration of 50 mg per ml. However, biofilm-related properties of the purified benzophenones have not been reported previously. This specification describes an unusual activity of xanthochymol and garcinol against *C. albicans* biofilms. Specifically, both xanthochymol and garcinol are cytotoxic to biofilms and target the hyphal form of fungus. The ability of these compounds to delay the emergence of germ tubes under biofilm inducing conditions is an important outcome, because the yeast-hyphal transition is strongly linked to the establishment of *C. albicans* infection and cell and tissue damage. Once the germination program was initiated, xanthochymol did not initially prevent growth or branching of the hyphae. However, the compounds were cytotoxic to the developed hyphae over the course of 9 to 12 h.

Xanthochymol did not significantly affect the attachment of the cells to glass slides coated with fibronectin. However, after 3 h of treatment, it was apparent that the attached cells failed to form germ tubes and appeared to be locked in the yeast form of the growth. Referring to FIGS. 1A to 2D, the effects of xanthochymol on early biofilm development is shown over time. FIG. 1A, FIG. 1B, FIG. 1C and FIG. 1D show inhibition of *C. albicans* hyphae and biofilm in the presence of xanthochymol (35 μg per ml) at 1.5 hours, 3 hours, 9 hours and 24 hours from adhesion, respectively. FIGS. 2A to 2D show normal biofilm development in corresponding controls that lacked xanthochymol. Small arrows (FIG. 1B and FIG. 1C) denote chains of yeast cells. Note the microcolonies apparent in the control culture at 3 hours (FIG. 2B) and 9 hours (FIG. 2C) denoted by the large arrows. The fungus did not overcome the xanthochymol-induced block of the morphological switch even after 24 h under biofilm-inducing conditions. Under these conditions, some yeast cells formed short linear chains, but there were few germ tubes, and the culture never developed true hyphae. In the presence of xanthochymol, the fungi also failed to form microcolonies. Garcinol (70 μg per ml) also inhibited germ tube emergence after adhesion but, unlike results with xanthochymol, the inhibition was transient, and germ tubes sometimes emerged after 6 h. When germ tubes were allowed to emerge before treatment with xanthochymol, the germ tubes elongated and branched for several hours. In contrast, when *C. albicans* DAY185 planktonic cells were grown in YPD in the presence or absence of either *Garcinia* benzophenone (70 μg per ml), there was no significant effect on the growth or viability.

In one embodiment, a method of treating an inanimate surface is provided such that growth of fungi on the inanimate surface is inhibited. In one such embodiment, an aqueous solution comprising at least 1 microgram per mL of a catechol is applied to the surface, wherein the catechol has a structure consistent with:

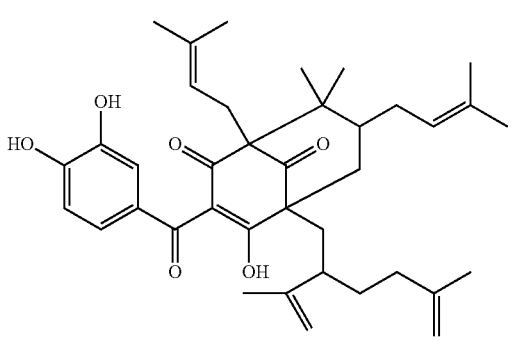 [SMILES: C=C(C)CCC(CC12CC(CC=C(C)C)C(C)(C)C(CC=C(C)C)(C(=O)C(C(=O)c3ccc(O)c(O)c3)=C1O)C2=O)C(=C)C]

The catechol may be xanthochymol, garcinol or a combination of both. In one such embodiment, the solution consists essentially of the polyisoprenylated benzophenone and may also include additional components (e.g. stabilizers, buffers, and the like) that do not materially alter the antifungal properties. In one embodiment, the concentration of the catechol is at least 1 microgram per mL and less than 50 mg per mL. In another embodiment, the concentration of the catechol is at least 1 microgram per mL and less than 25 mg per mL. The application may occur early in the lifecycle of the fungi (e.g. within 12 hours, 9 hours, or 3 hours of attachment of the fungi to the surface). Treatment times may vary (e.g. for at least one hour or for at least three hours). The composition may also be used to treat a biological organism (e.g. a plant or an animal) that has been exposed to fungi. For animal treatments, the composition may be administered orally (e.g. as a tablet, capsule, etc.), topically or intravenously as an aqueous solution. For plant treatments, the composition may be administered applied environmentally (e.g. sprayed), topically or by injection. In one embodiment, the composition has an EC50 of less than 100 µM against *Candida albicans*.

In summary, xanthochymol and garcinol showed multiple activities against *Candida albicans*. Concentrations in the low micromolar range inhibited germ tube emergence and development of true hyphae. Intervention against early biofilms resulted in cytostatic and apoptosis-like responses. These activities are consistent with a possible function as an inhibitor of the fungal dimorphic switch. In mature biofilms, the compounds induced hypha-specific death, an action that could lead to the disruption and removal of the biofilm. Such activity should ameliorate hypha-induced cell and tissue damage in candidiasis. Furthermore, xanthochymol potentiated the activity of fluconazole. Therefore, these studies highlight the possible use of xanthochymol as well as garcinol in apoptosis studies and antifungal drug discovery.

SUMMARY OF EXPERIMENTALS

*Candida albicans* formed biofilms during incubation in RPMI medium at a pH of 7.0 and at 37° C. for 24 h. These biofilms were then treated with xanthochymol or garcinol at 70 µg per ml for a further 24 h. LIVE/DEAD staining of the biofilm was performed and dead cells were quantified in confocal micrographs. In the presence of xanthochymol or garcinol, large propidium iodide-positive areas were evident, characteristic of inviable cells with leaky membranes. Close examination of treated biofilms showed that both compounds were effective at killing hyphae present in the mature biofilm, whereas the yeast form cells were Syto-9 positive, indicating they were viable. As a positive control, caspofungin (0.06 µg per ml) showed killing of planktonic yeast phase cells but was less effective against a biofilm.

The LIVE/DEAD staining was also used to determine whether the benzophenones could kill the biofilm cells during development or whether benzophenone activity was only cytostatic. Treatment of *C. albicans* biofilms (70 µg per ml) after attachment but before germ tube emergence precluded hyphal development for 24 h. Although there were clumps of yeast in the treated cultures, the biofilms were devoid of true hyphae in the xanthochymol-treated samples. The cells in these biofilms remained substrate attached, but many were killed by the drug. In the presence of garcinol, some germ tubes were observed, but the majority of cells in the culture were loosely attached or floating, indicating cell-cell aggregation but not cell-substratum attachment. Fewer cells were killed during garcinol treatment.

To assess the minimum concentrations of xanthochymol for perturbation of early biofilms, a dose-response analysis was carried out by adding xanthochymol to biofilms after 3 h of development. Xanthochymol concentrations in the low micro-molar range (8.8 µg per ml, 13 µM) effectively induced cell death after 9 h of drug treatment. Lower concentrations were cytostatic, with clear indications of hyphal inhibition at MICs near 1 µg per ml. Garcinol had similar activity.

To determine the activities of xanthochymol against mature biofilms, mature biofilms were treated with xanthochymol for 24 h and then stained for cell viability. There was massive death of hyphae at concentrations of 35 µg per ml and greater. Incidentally, xanthochymol treatment did not affect XTT reduction of the biofilm, perhaps because mitochondrial function is severely downregulated in the biofilm state.

These results demonstrated the fungistatic and fungicidal activity in early biofilms after hyphal emergence, with an MIC of 1 µg per ml (1.6 µM) and a fungicidal $IC_{80}$ of 8.8 µg per ml (13 µM). Cell death resulting from xanthochymol treatment of *C. albicans* appeared to be similar to its caspase-dependent apoptotic effects in human cancer cells. Xanthochymol-treated biofilms showed externalization of PS and DNA cleavage, as evidenced by TUNEL fluorescence. The presence of TUNEL-positive cells speaks to the involvement of a caspase-like mechanism similar to that mediated by the *C. albicans* metacaspase Mca1 in response to oxidative stress. This metacaspase-dependent system is also activated in response to treatment with resveratrol, curcumin, propolis, amphotericin B, and caspofungin. These results suggest that the *Garcinia* benzophenones described in this specification have the characteristics of metacaspase-dependent activators of apoptosis in *C. albicans* biofilms.

Treatment of Animals

In another embodiment, nematode *Caenorhabditis elegans*, a model animal host for fungal infections, was exposed to *Candida albicans* for 4 hours, then cultured in the presence or absence of xanthochymol 140 µg per ml. Within 24 hours, 4 of 10 nematodes treated without xanthochymol were dead, and all were dead by 48 hours, with extensive disruption of the nematode cuticles by fungal hyphae. In contrast, 50% of nematodes treated with xanthochymol remained alive and several had no hyphae visible.

Mechanism of Action

Without wishing to be bound to any particular theory, the observed cell death in the disclosed biofilms may be apoptotic in nature. Biofilms were developed for 3 h after adhesion, then treated without or with xanthochymol at 17.5 µg per ml for 3 h. To determine if features of apoptosis were present, the presence of DNA fragmentation was first verified with TUNEL staining, which was apparent in xanthochymol-treated cultures but not in the untreated samples. An assay was also conducted for phosphatidyl serine (PS) externalization, as evidenced by binding of annexin V. The presence of annexin V staining indicated intact plasma membranes in C. albicans biofilms after the 3 h of xanthochymol treatment, indicating early apoptosis. Propidium iodide counterstaining showed some yeast and hyphae with disrupted membranes and necrotic cell death as well. Thus, xanthochymol effects on early biofilms included induction of both apoptotic-like, induction of cytostasis, and some cytotoxicity in yeast phase cells, depending on the xanthochymol dose and duration of exposure.

Combination Treatments

There was complementarity in the activities of xanthochymol and fluconazole. Fluconazole inhibits production of hyphae and hypha-specific wall proteins. The data show similarity in that xanthochymol-inhibited hyphal development. Therefore, the compounds may reinforce each other's activities. In contrast, caspofungin increases the expression of hypha-specific proteins, an antagonistic result. These assays have shown antagonism in efficacy assays of xanthochymol with caspofungin.

Given that C. albicans within a biofilm can be up to 1,000-fold more resistant than planktonic yeast to fluconazole, and given the specificity of xanthochymol for hyphae, the two compounds were tested complementary antifungal activities. The combination of fluconazole and xanthochymol was tested at 3 h and 24 h of biofilm development. In early biofilms, fluconazole at 32 µg per ml reduced biofilm activity by 20% (FIG. 3). Xanthochymol at 4 µg per ml reduced biofilm activity 65%. The effect of adding both drugs together was additive, resulting in a significant reduction in biofilm viability.

Established C. albicans DAY185 biofilms are markedly resistant to fluconazole. The 24-h biofilms showed only a 15% reduction in viability at fluconazole concentrations as high as 1,024 µg per ml by XTT assay (data not shown). Xanthochymol and fluconazole was therefore tested in combination. After 24 h of growth, biofilms were treated with fluconazole, xanthochymol, or both drugs together. Following 24 h of exposure to the compounds, the biofilms were assayed by microscopy. As a single agent, fluconazole had minimal effect, whereas xanthochymol effectively killed hyphae. The combination of fluconazole with xanthochymol killed most of the cells in the biofilm. Furthermore, the confocal micrographs showed the death of almost all hyphae, and many of the yeasts co-stained with both dyes; the nonred cells were markedly yellow compared to those in the control biofilm or the biofilms treated with fluconazole or xanthochymol alone. The yellow color is consistent with the remaining biofilm cells being in the process of dying. Double dilution assays showed that xanthochymol at 50 µg per ml reduced the fluconazole $IC_{50}$ to 13 µg per ml. Therefore, the drug combination was more effective than either drug alone and was toxic to all of the biofilm cells.

Combination treatments other than catechol/fluconazole are also contemplated. Other suitable antifungal agents can also be used in combination with the catechol including, but not limited to, azoles, echinocandins, amphotericin or nucleotide derivatives. The antifungal agent may be administered simultaneously, before (e.g. within three hours), or after (e.g. within three hours) of treatment with the catechol.

Materials and Methods

Candida albicans Strain and Growth Medium.

Candida albicans strain DAY185 (ura3D::imm434/Iura3D::imm434HIS1::hisG/his1::hisG ARG4::URA3::arg4::hisG/arg4::hisG) forms robust biofilms and is resistant to the antifungal drug fluconazole; therefore, this strain was used in this study. Candida albicans was subcultured onto Sabouraud dextrose agar (per liter: peptone 10 g, dextrose 40 g, agar 15 g; pH of 5.6) and incubated at 30° C. for 24 h. One colony was then added to yeast extract-peptone-dextrose (YPD; 1% yeast extract, 2% peptone, 2% dextrose) and incubated with shaking at 30° C. and 170 rpm for 16 h, after which cells were harvested, washed in phosphate-buffered saline (PBS), and diluted to a standard inoculum of $1.0 \times 10^6$ cells per ml.

Garcinia Compounds.

Garcinol was obtained from Cayman Chemical. The purity of the compound was greater than 95%. Xanthochymol was isolated from a methanol extract from Garcinia xanthochymus fruits by reverse-phase column chromatography. Chemical structures were determined by one-dimensional and two-dimensional nuclear magnetic resonance and mass spectrometry. The purity of xanthochymol in all experiments was greater than 99%, as determined by high-pressure liquid chromatography (HPLC).

Established Biofilm Assays.

For biofilm assays in microtiter plates, 100 µl of a standard inoculum of C. albicans cells ($1.0 \times 10^6$ cells per ml) was added to the wells of a 96-well plate in triplicate, and the cells were allowed to adhere for 90 min at 37° C. After incubation, the plates were washed twice with PBS to remove nonattached cells. Then 100 µl of RPMI 1640 with L-glutamine, without sodium bicarbonate (GIBCO®), buffered to pH 7.0 with 165 mM morpholinepropanesulfonic acid (MOPS) was added to each well, and the plates were incubated at 37° C. for 24 h. Early-stage biofilms were prepared essentially as above, with the exception that the cells were induced to form biofilms for either 3 or 6 h prior to treatment.

Susceptibility Testing of Candida Biofilms.

Fluconazole was obtained from Sigma. All drugs were dissolved in dimethyl sulfoxide (DMSO). After overnight growth of biofilms, plates were carefully washed to remove nonadherent cells, and then 100 µl of 2-fold dilutions of xanthochymol and/or fluconazole, prepared according to Clinical and Laboratory Standards Institute guidelines, was added to the wells; then, the plates were returned to the incubator for a further 24 h.

Colorimetric Readout Based on XTT.

Menadione and XTT [2,3-bis-(2-methoxy-4-nitro-5-sulfophenyl)-2H-tetrazolium-5-carboxyanilide] were obtained from Sigma-Aldrich. After a drug challenge, the wells were washed twice with PBS, and then 100 µl of XTT-menadione solution was added to the wells, and plates incubated in the dark for 1 h at 37° C. The absorbance of wells at 490 nm was read using a microplate reader (Biotec/Synergy software).

Confocal Microscopy.

Candida albicans biofilms were treated with or without test compounds for various times, depending on the experimental design, after which the cells were prepared for microscopy by staining with the BacLight yeast viability kit, the contents of which include Syto-9 and propidium iodide (Molecular Probes, Eugene, Oreg.) according to the manufacturer's instructions. Confocal images were obtained using an Olympus FluoView10i microscope and a filter set for Syto-9 and propidium iodide. Overlays included phase contrast images. All confocal images were processed using ImageJ.

Time Lapse Imaging.

Bright-field images were obtained using an Olympus CKX41 cell culture microscope, attached to a Bioflux 200 automated microfluidic system for live cell imaging (Flux-ion Biosciences, Inc.). Images were acquired using the Bioflux 200 camera driven by the Bioflux 200 software. All images were acquired using the 10× objective with a zoom factor of 0.5.

Annexin V Assays.

Protoplasts of *C. albicans* early biofilms were obtained by incubation of the biofilm in potassium phosphate buffer (50 mM $K_2HPO_4$, 5 mM EDTA, 50 mM dithiothreitol [DTT]), followed by treatment with 0.02 mg per ml zymolase (Sigma-Aldrich) for 10 min at 30° C. Protoplasts were washed and permeabilized on ice for 2 min in 0.1 M sodium citrate buffer containing 0.1% Triton X-100. The sphero-plasts were stained with fluorescein isothiocyanate [FITC]-labeled annexin (Roche) according to the manufacturer's directions.

Terminal Deoxynucleotidyltransferase-Mediated dUTP-Biotin Nick End Labeling Staining.

Detection of DNA breakage, was accomplished using the In Situ Cell Death detection kit (Roche Life Sciences) according to the manufacturer's instructions. Briefly, biofilms were washed in PBS, followed by fixation in 4% paraformaldehyde for 1 h at 4° C. After fixation, biofilms were subjected to digestion with 0.02 mg per ml zymolase for 10 min at 30° C., followed by careful washing with PBS. Digested biofilms were permeabilized as indicated above and then incubated with 50 µl of terminal deoxynucleotidyl transferase mediated dUTP-biotin nick end labeling (TUNEL) reaction mixture for 1 h at 37° C.

Calculations.

Biofilm viability was assayed by XTT reduction and calculated as follows:

$$\% \text{ viability} = \frac{100 \times (ABS_{well} - ABS_{background})}{(ABS_{untreated\ wells} - ABS_{background})}$$

where background wells contained XTT solution only; untreated wells received cells only, with no added drug. The $EC_{50}$ and 80% inhibitory concentration ($IC_H$) values were intercalated from the dose-response curves. The MIC was defined as the lowest concentration of drug capable of inhibiting growth, as measured by XTT assay, or the minimum concentration showing a significant increase in killing in the LIVE/DEAD assays.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of treating a surface to inhibit biofilm formation, the method comprising
    applying a composition of matter to an inanimate surface to inhibit growth of a fungal species on the inanimate surface, the composition of matter comprising a catechol having a structure given by:

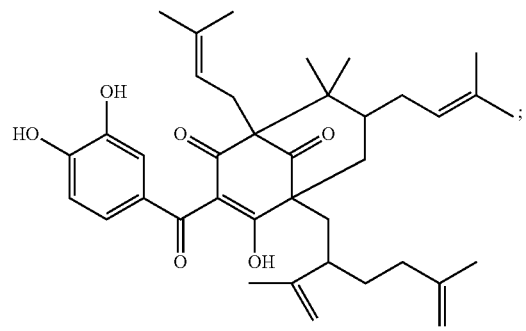 [SMILES: C=C(C)CCC(CC12CC(CC=C(C)C)C(C)(C)C(CC=C(C)C)(C(=O)C(C(=O)c3ccc(O)c(O)c3)=C1O)C2=O)C(=C)C]

wherein the composition of matter further comprises a combination of fluconazole and the catechol wherein the combination reduces a 50% effective concentration ($EC_{50}$) of the combination by at least 50% relative to fluconazole alone;
permitting the catechol to remain in contact with the fungal species for at least three hours at a concentration of at least 1 microgram per mL to inhibit the fungal species from forming a biofilm.

2. The method as recited in claim 1, wherein the concentration is at least 1 microgram per mL and less than 50 mg per ml.

3. The method as recited in claim 1, wherein the step of applying occurs within twelve hours of the fungal species attaching to the inanimate surface.

4. The method as recited in claim 1, wherein the step of applying occurs within nine hours of the fungal species attaching to the inanimate surface.

5. The method as recited in claim 1, wherein the step of applying occurs within three hours of the fungal species attaching to the inanimate surface.

6. The method as recited in claim 1, wherein the structure of the catechol is given by:

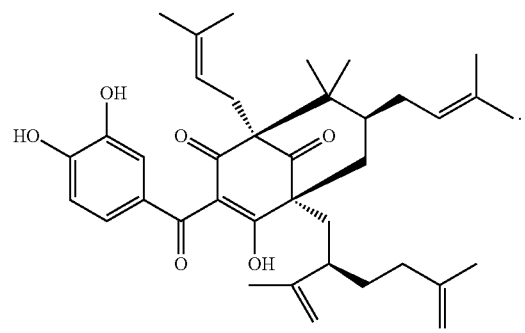 [SMILES: C=C(C)CC[C@H](C[C@]12C[C@H](CC=C(C)C)C(C)(C)[C@](CC=C(C)C)(C(=O)C(C(=O)c3ccc(O)c(O)c3)=C1O)C2=O)C(=C)C]

7. The method as recited in claim 1, wherein the fungal species is *Candida albicans*.

8. The method as recited in claim 1, wherein the composition of matter is an aqueous solution.

9. The method as recited in claim 1, further comprising determining that the inanimate surface has the fungal species and thereafter performing the step of applying.

10. A method of treating a biological organism to inhibit biofilm formation, the method comprising determining that a biological organism is infected by a fungal species;
    administering a composition of matter to the biological organism to inhibit growth of the fungal species, the composition of matter comprising a catechol having a structure given by:

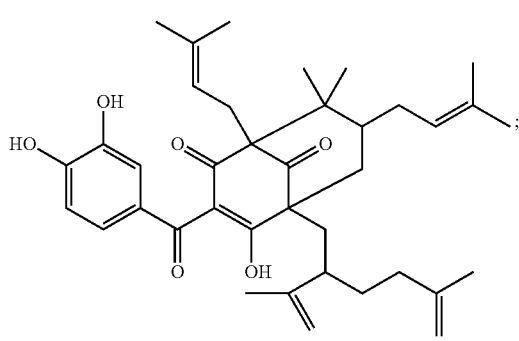 [SMILES: C=C(C)CCC(CC12CC(CC=C(C)C)C(C)(C)C(CC=C(C)C)(C(=O)C(C(=O)c3ccc(O)c(O)c3)=C1O)C2=O)C(=C)C]

wherein the composition of matter further comprises fluconazole;

permitting the catechol to remain in contact with the fungal species at a concentration of at least 1 microgram per mL for at least one hour to inhibit the fungal species from forming a biofilm.

11. The method as recited in claim 10, wherein the composition of matter has an 50% effective concentrations ($EC_{50}s$) of less than 100 μM against *Candida albicans*.

12. The method as recited in claim 10, wherein the biological organism is a plant.

13. The method as recited in claim 10, wherein the biological organism is an animal.

14. The method as recited in claim 10, wherein the fungal species is *Candida albicans*.

15. The method as recited in claim 10, wherein the structure of the catechol is given by:

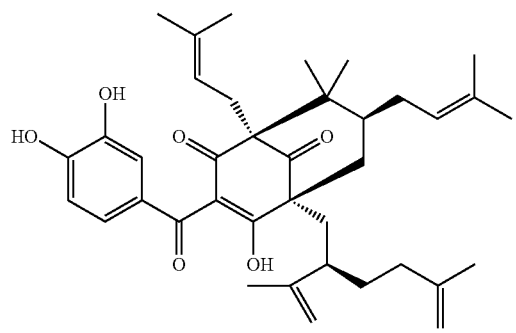

16. The method as recited in claim 1, wherein the concentration is at least 1 microgram per mL and less than 50 mg per ml.

17. The method as recited in claim 1, wherein the concentration is at least 1 microgram per mL and less than 25 mg per ml.

* * * * *